US010993982B2

(12) United States Patent
Atlasman et al.

(10) Patent No.: US 10,993,982 B2
(45) Date of Patent: May 4, 2021

(54) COMPOSITIONS COMPRISING HEAT-TREATED CLEAR TOMATO CONCENTRATE

(71) Applicant: LYCORED LTD., Beer-Sheva (IL)

(72) Inventors: Tatyana Atlasman, Beer-Sheva (IL); Yoav Blatt, Rehovot (IL); Rachel Levy, Omer (IL); Yoav Sharoni, Omer (IL); Joseph Levy, Omer (IL); Morris Zelkha, Ramat-Ga (IL)

(73) Assignee: LYCORED LTD., Beer Sheva (IL)

( * ) Notice: Subject to any disclaimer, the term of this patent is extended or adjusted under 35 U.S.C. 154(b) by 285 days.

(21) Appl. No.: 14/762,343

(22) PCT Filed: Jan. 22, 2014

(86) PCT No.: PCT/IL2014/050075
§ 371 (c)(1),
(2) Date: Jul. 21, 2015

(87) PCT Pub. No.: WO2014/115140
PCT Pub. Date: Jul. 31, 2014

(65) Prior Publication Data
US 2015/0352169 A1 Dec. 10, 2015

Related U.S. Application Data

(60) Provisional application No. 61/754,975, filed on Jan. 22, 2013, provisional application No. 61/754,976, filed on Jan. 22, 2013.

(51) Int. Cl.
A61K 36/81 (2006.01)
A61K 31/01 (2006.01)
A61K 31/05 (2006.01)
A23L 33/105 (2016.01)
A23L 33/175 (2016.01)
A23L 33/15 (2016.01)

(52) U.S. Cl.
CPC ............ A61K 36/81 (2013.01); A23L 33/105 (2016.08); A23L 33/15 (2016.08); A23L 33/175 (2016.08); A61K 31/01 (2013.01); A61K 31/05 (2013.01); A23V 2002/00 (2013.01); A61K 2236/00 (2013.01)

(58) Field of Classification Search
None
See application file for complete search history.

(56) References Cited

U.S. PATENT DOCUMENTS 5,837,311 A 11/1998 Zelkha et al.
6,890,574 B1 5/2005 Geifman et al.
2006/0286187 A1 12/2006 Bortlik et al.
2009/0053340 A1 2/2009 Crosbie et al.
2009/0264291 A1 10/2009 Soudant et al.
2010/0183537 A1 7/2010 Bortlik et al.
2010/0196563 A1 8/2010 Zelkha et al.
2012/0071550 A1 3/2012 Zelkha et al.

FOREIGN PATENT DOCUMENTS

JP 2008-303166 12/2008
WO WO 2005/105131 11/2005

OTHER PUBLICATIONS

Matulka et al. (2004) Regulatory Toxicology and Pharmacology 39: 390-402 (Year: 2004).*
Story et al. (2010) Annu. Rev. Food Sci. Technol. 2010; 1:.doi:10.1146/annurev.food.102308.124120 (24 pages) (Year: 2010).*
Dewanto et al., "Thermal Processing Enhances the Nutritional Value of Tomatoes by Increasing Total Antioxidant Activity," *Journal of Agricultural and Food Chemistry*, 2002, vol. 50, pp. 3010-3014.
Veed "How to make tomato water" Publication (online) Jun. 18, 2010; <https://web.archive.org/web/20110306160337/htto://www.seriouseats.com/2010/06/how-to-make-tomato-water.html>.
Rafi et al., "Dietary lutein modulates inducible nitric oxide synthase (iNOS) gene and protein expression in mouse macrophage cells (RAW 264.7)," *Molecular Nuitrition & Food Research*, 2007, vol. 51, pp. 333-340.
Choi et al, "Inhibition of nNOS and COX-2 expression by lutein in acute retinal ischedmia," *Nutrition*, 2006, vol. 22, pp. 668-671.
Rafi et al., Lycopene Inhibits LPS-Induced Proinflammatory Mediator Inducible Nitric Oxide Synthase in Mouse Macrophage Cells, *Journal of Food Science*, 2007, vol. 72, No. 1, pp. S69-S74.
International Search Report issued in Application No. PCT/IL14/50075 dated Jun. 2, 2014.
Thaiphanit et al., "Physicochemical and emulsion properties of edible protein concentrate from coconut (*Cocos nucifera* L.) processing by-products and the influence of heat treatment" *Food Hydrocolloids*, vol. 52: 756-765 (2016).
Wolfs et al., "HIV-Antibody Seroconversions in Dutch Haemophiliacs Using Heat-Treated and Non Heat-Treated Coagulation Factor Concentrates" *Thrombosis and Haemostasis*, vol. 59, No. 3: 396-399 (1988).
Mahsa et al., Effect of tomato juice on serum concentrations of IL-6, IL-8, CRP and TNF-α in female students' overweight or obese dormitory of Tehran University of Medical Sciences, Clinical Biochemistry 44 (13): S81 (Aug. 2011).
Mahsa et al., Tomato juice consumption reduces systemic inflammation in overweight and obese females, British Journal of Nutrition (2013), 109, 2031-2035.
Journal of Japanese Society for Bone and Mineral Research, 2007 vol. 25, p. 228.

* cited by examiner

*Primary Examiner* — Russell G Fiebig
(74) *Attorney, Agent, or Firm* — Nixon & Vanderhye P.C.

(57) ABSTRACT

The present invention provides a therapeutic composition comprising heat-treated clear tomato concentrate (CTC), which has been found to possess both anti-inflammatory and bone-health promoting effects. The present invention is also directed to a composition comprising heat-treated CTC in combination with one or more carotenoids.

14 Claims, 12 Drawing Sheets

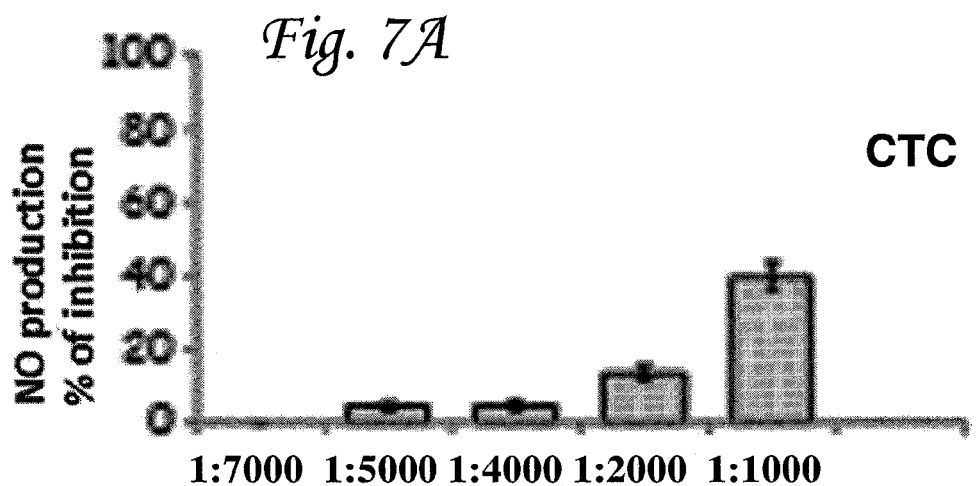
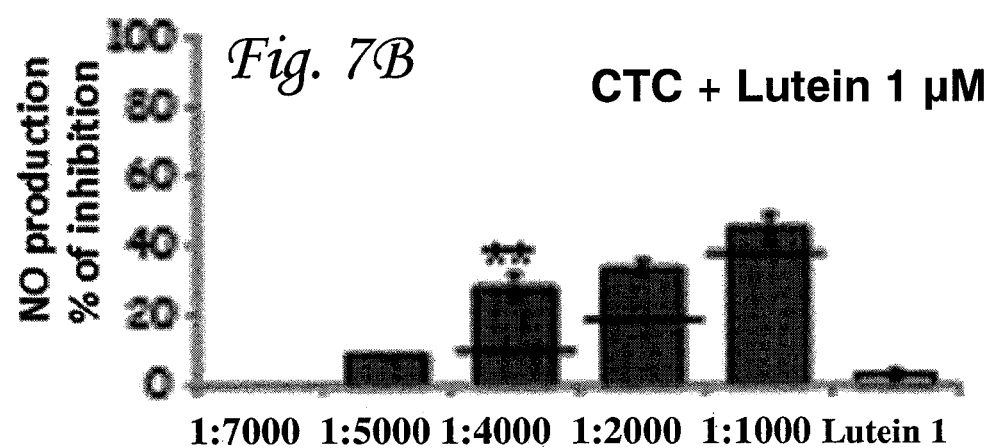
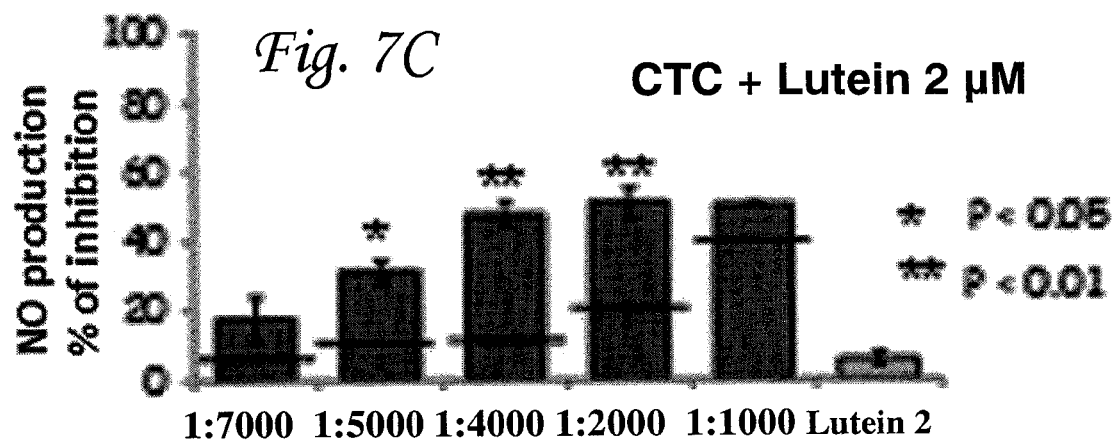

COMPOSITIONS COMPRISING HEAT-TREATED CLEAR TOMATO CONCENTRATE

This application is the U.S. national phase of International Application No. PCT/IL2014/050075 filed 22 Jan. 2014 which designated the U.S. and claims the benefit of U.S. Provisional Application Nos. 61/754,975 filed 22 Jan. 2013, and 61/754,976 filed 22 Jan. 2013, the entire contents of each of which are hereby incorporated by reference.

FIELD OF THE INVENTION

The present invention relates to a composition comprising a heat-treated tomato-derived concentrate which has been found to possess an unexpectedly high level of anti-inflammatory activity. The present invention is also directed to a synergistic combination of a heat-treated tomato-derived concentrate with carotenoids.

BACKGROUND OF THE INVENTION

The inflammatory process, which forms an important part of the non-specific immune system, is characterized by a complex set of chemical and cellular changes that are essential for host defense in the face of microbial agents and other potentially harmful environmental factors. However, in many cases, inflammation may be triggered inappropriately, and/or may persist to a degree which becomes harmful to the host. In such cases, there may be a need to inhibit or prevent the development of one or more aspects of the inflammatory process, in particular, in cases of non-infectious inflammatory diseases.

A very large number of different chemical mediators have been shown to be involved in the development and control of the inflammatory process. Recent studies by a number of different laboratories have implicated nitric oxide (NO) as an important modulator of a variety of acute and chronic inflammatory disorders, including various types of arthritis, gastro-intestinal diseases, inflammatory conditions of the central nervous system and certain forms of asthma. Consequently, it has been proposed that inhibition of NO production could provide a useful therapeutic mechanism for the treatment and/or management of these inflammatory disorders. Furthermore, inhibition of NO synthesis has also been shown to be useful in some conditions or states that are not primarily inflammatory in nature. Thus, for example, inhibition of NO synthesis has been found to reduce glucose uptake into limb tissue in individuals with Type 2 diabetes during exercise.

The in vivo production of NO is mediated by a family of nitric oxide synthase (NOS) enzymes, including inducible-nitric oxide synthase (I-NOS), which is activated by many different immunological stimuli including lipopolysaccharide (LPS), interferon gamma and interleukin 1 (IL-1).

Inhibition of NO may be achieved both in vitro and in vivo by the use of L-N$^G$-monomethyl Arginine citrate (L-NMMA). In addition, several other compounds, including a number of natural products, have also been shown to inhibit NO production. The latter group includes compounds such as lutein [Rafi M. M. et al. *Mol Nutr Food Res.* 2007 March; 51 (3):333-40; Choi, J. S. *Nutrition.* 2006 June; 22 (6):668-71] and lycopene [Rafi, M. M. et al. *J Food Sci.* 2007 January; 72 (1):S069-74]. However, the efficacy and potency of many of the natural product NO inhibitors have proven to be not particularly high. A need therefore exists for improved NO production-inhibiting compositions of natural origin.

Another highly important inflammatory mediator is tumor necrosis factor-alpha (TNF-alpha), which is a cytokine produced by a variety of cell types including macrophages, neutrophils and lymphocytes. TNF-alpha occupies a key position in the early stage of the inflammatory process and is responsible for stimulating the production of other factors such as nuclear factor-κB which in turn causes activation of a wide range of pro-inflammatory genes. Thus, in view of its key pro-inflammatory role, TNF-alpha is clearly an important potential therapeutic target for anti-inflammatory agents.

Turning now to another aspect, in order to preserve healthy, normal bone structure, bone is continually subjected to remodeling, wherein bone is broken down by osteoclasts and re-built by osteoblasts.

The differentiation of osteoclasts is influenced inter alia by RANKL (receptor activator of NFKB ligand), a cytokine produced by osteoblasts, which binds to osteoclast progenitor cells. Inhibition of this process would lead to a reduction in osteoclastic activity, and thereby inhibit bone resorption.

An alternative strategy for altering the balance between bone resorption and the product of new bone in the bone remodeling process would be to cause increased osteoblast activity. While this result may potentially be achieved in several ways, one possible route is via activation of anti-oxidant response element (ARE/Nrf2) signaling in osteoblasts.

An imbalance between bone formation and bone resorption can lead to the development of pathological conditions such as osteoporosis, arthritis, periodontal disease, multiple myeloma and metastatic cancers. For individuals with osteoporosis, bone fractures represent life-threatening events, and today there are in excess of 70 million people worldwide at risk.

In cases of excessive bone resorption (such as occurs in osteoporosis), it would be advantageous to be able to alter the balance between resorption and the laying down of new bone. Ideally, this would be achieved by the use of a natural, non-toxic substance that is substantially free of adverse effects. One of the aims of the present invention is to meet this need.

One purpose of the present invention to provide a natural product composition that may be used to inhibit the production of one or more key inflammatory mediators, such as NO and TNF-alpha, as a means for treating or managing pathological states and processes in which said mediators are implicated.

It is another purpose of the present invention to provide a tomato-derived composition having improved anti-inflammatory properties.

A still further purpose of the present invention is to provide a natural product composition for improving bone health.

Other aims and purposes will become apparent as the description proceeds.

SUMMARY OF THE INVENTION

It has now been found by the present invention that the anti-inflammatory properties of a tomato-derived product known as clear tomato concentrate (CTC) are enhanced by subjecting said CTC to heat treatment prior to use.

The term "CTC" refers to concentrated tomato serum that is obtained by means of separating tomato material (such as crushed tomatoes or tomato juice) into pulp and serum, discarding the pulp and then concentrating said serum to a Brix value between about 40 and 80, preferably above 55° Bx. The concentrated serum is referred to as "CTC". Further details of the preparation of CTC will be provided herein below.

The present invention is therefore primarily directed to a therapeutic composition comprising heat-treated CTC.

While several different heating regimes may be used to prepare the aforementioned heat-treated CTC, in one preferred embodiment, the CTC (at a concentration corresponding to approximately 60 Bx) is heated at 90 degrees C. for a period of between 1 and 3 hours. In a particularly preferred embodiment, heat-treated CTC is prepared by heating CTC for 1 hour at 90 degrees C.

In one preferred embodiment, the therapeutic composition of the present invention consists essentially of heat treated CTC.

It is to be noted that the term "consists essentially of", as used throughout this disclosure and appended claims refers to the situation wherein the composition of the present invention may comprise, in addition to the primary active substance (heated CTC), other compounds, substances and agents which do not materially affect the basic novel and inventive characteristics of the present invention.

In one preferred embodiment, the above-disclosed composition comprising heat-treated CTC has a total free amino acid concentration that is less than 2% w/w. Also, the free glutamine concentration of the composition comprising heat-treated CTC is preferably less than 0.1% w/w.

Furthermore, it has now been unexpectedly found that heated CTC interacts synergistically with carotenoids, thereby producing an enhanced anti-inflammatory effect. The present invention is therefore further directed to a therapeutic composition comprising a synergistic combination of heat-treated CTC and one or more carotenoids.

In one preferred embodiment of this combination composition, the total free amino acid concentration is less than 2% w/w. Similarly, the free glutamine concentration is preferably less than 0.1% w/w.

While many different carotenoids may be incorporated into the composition of the present invention, in a preferred embodiment, said composition comprises one or more carotenoids selected from the group consisting of lycopene, phytoene, phytofluence, beta-carotene and lutein, and/or their derivatives. However, it is to be recognized that many other carotenoids may also be used to prepare the synergistic compositions of the present invention.

In a particularly preferred embodiment, the composition of the present invention comprises heated CTC and tomato oleoresin, wherein said oleoresin comprises the carotenoids lycopene, phytoene, phytofluence and beta-carotene. A commercially-available example of such a tomato oleoresin is Lyc-O-Mato®, manufactured and supplied by the applicant, LycoRed Ltd. of Be'er Sheva, Israel.

In one preferred embodiment, the therapeutic composition of the present invention consists essentially of a synergistic combination of heat treated CTC and one or more carotenoids. In a particularly preferred embodiment, the therapeutic composition consists essentially of a synergistic combination of heat treated CTC and one or more carotenoids selected from the group consisting of lycopene, phytoene, phytofluence, beta-carotene and lutein. In one particularly preferred embodiment, the combination composition comprises lycopene. Most preferably, the composition consists essentially of heat treated CTC and tomato oleoresin.

Preferably, the total concentration of the carotenoids in the combination composition is at least 0.1% (w/w). In another preferred embodiment, wherein the carotenoids include lycopene, the concentration of said lycopene is at least 0.1% (w/w).

The present invention also relates to combinations of one or more carotenoids (as disclosed hereinabove) together with a modified CTC having a chemical and/or biochemical composition similar to that of the heat-treated CTC defined hereinabove or to said modified CTC alone. Thus, in one aspect, the present invention is directed to a therapeutic composition comprising a synergistic combination of one or more carotenoids together with CTC having a total free amino acid concentration of less that 2% w/w. In another embodiment, the application is directed to a therapeutic composition comprising a synergistic combination of at least one carotenoid together with CTC having a free glutamine concentration of less than 0.1% w/w.

In another aspect, the present invention provides a method for inhibiting or reducing the production of one or more anti-inflammatory mediators in a subject, as a means for treating or managing pathological states and processes in which said mediator is implicated, wherein said method comprises administering to said subject a therapeutic composition according to any of the embodiments disclosed hereinabove. While said method may be used to inhibit the production of many different inflammatory mediators, in one preferred embodiment, the anti-inflammatory mediator is selected from the group consisting of NO, TNF-alpha and interleukin 1.

In a further aspect, the present invention is directed to the use of heat-treated CTC in the manufacture of a medicament for the treatment of conditions responsive to inhibition of inflammatory mediators, particularly NO, TNF-alpha and/or interleukin 1.

In a further aspect, the present invention is directed to the use of heat-treated CTC and one or more carotenoids in the manufacture of a medicament for the treatment of condition responsive to inhibition of NO, TNF-alpha and/or interleukin 1.

In a still further aspect, the present invention is directed to the use of any of the compositions disclosed hereinabove in the manufacture of a medicament useful for improving bone health. In one preferred embodiment, said medicament is capable of inhibiting bone resorption, and may be used in the prevention, treatment or management of conditions such as (but not limited to) osteoporosis, arthritis, periodontal disease, multiple myeloma and metastatic cancers.

Furthermore, the present invention also provides a method of treatment of pathological conditions in which NO, TNF-alpha and/or interleukin 1 act as a modulators or mediators of said condition is a subject in need of such treatment, wherein said method comprises administering to said subject a therapeutic composition according to any one of the embodiments disclosed hereinabove. In one preferred embodiment of this method, the condition to be treated is selected from the group consisting of acute inflammatory conditions, chronic inflammatory conditions, rheumatoid arthritis, adult respiratory distress syndrome (ARDS), asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis, peritonitis and inflammatory bowel disease, and neurodegenerative diseases, such as for example Alzheimer's disease (AD).

In one preferred embodiment, the condition to be treated is an inflammatory condition.

In another aspect, the present invention is directed to a method for improving bone health in a subject, comprising administering to said subject a therapeutic composition as disclosed hereinabove.

In one preferred embodiment of this aspect, the improvement in bone health comprises the inhibition of bone resorption. The method for improving bone health may be used in subjects having any condition or disease that will be used in subjects having any condition or disease that will respond thereto, including, but not limited to osteoporosis, arthritis, periodontal disease, multiple myeloma and metastatic cancers.

In preferred embodiments of the methods described hereinabove, the subject is a mammalian subject and more preferably a human subject.

While in the above-disclosed methods, the therapeutic composition may be administered by any convenient means, in one preferred embodiment said composition is administered in a pharmaceutical dosage form. In another preferred embodiment, however, the therapeutic composition is incorporated into a foodstuff or beverage.

All the above and other characteristics and advantages of the present invention will be further understood from the following illustrative and non-limitative examples of preferred embodiments thereof.

BRIEF DESCRIPTION OF THE DRAWINGS

FIG. 7 graphically represents the inhibition of NO production by peritoneal macrophages caused by lutein alone and heated CTC alone, with a combination of lutein and heated CTC.

DETAILED DESCRIPTION OF PREFERRED EMBODIMENTS

Figure 1A:
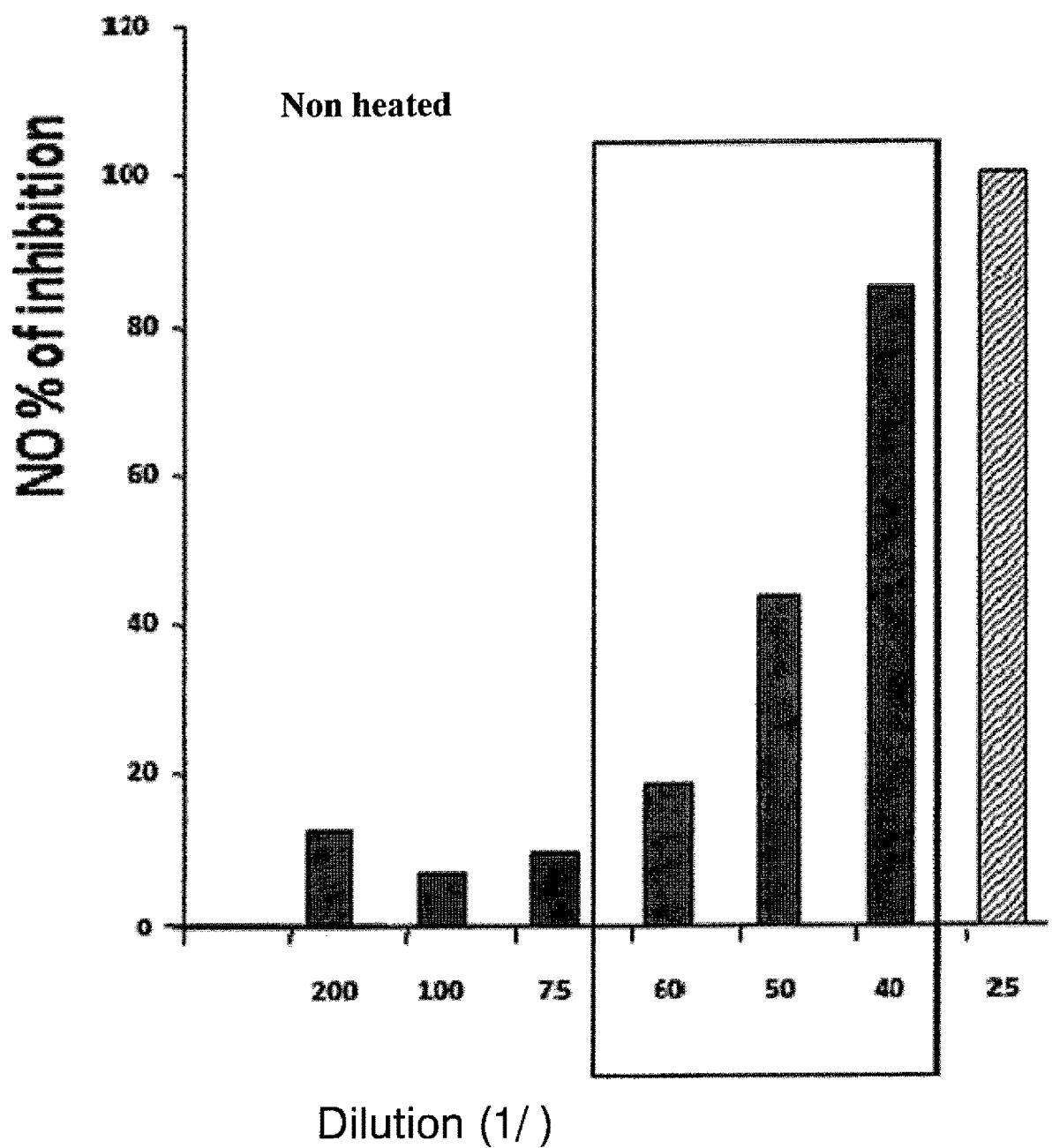
FIG. 1 graphically compares the inhibition of NO production by peritoneal macrophages by treatment regular, non-heated CTC (FIG. 1A) with that caused by treatment with heat-treated CTC (FIG. 1B).

As disclosed hereinabove, the present invention provides compositions comprising heat-treated CTC alone or combined with one or more carotenoids. The fraction known as CTC may typically (but not exclusively) be prepared by means of the following process:

Step 1: Tomatoes are washed and sorted according to their color and quality.

Step 2: Clean tomatoes are crushed; at this point the raw crushed tomatoes are sampled for lycopene content and sugar content.

Step 3: Raw crushed tomatoes are screened through 4-6 and 12 mm nets.
   Additional step 3.1: Water is added to the retained solids are further screened on 0.6 and 0.8 mm nets in order to remove peel particles.

Step 4: Slurry obtained from step 3 is further screened on 1.5 to 4 mm nets.

Step 5: Slurries from step 4 and 3.1 are pooled together and stored in a container; at this point the slurries are sampled and analyzed.

Step 6: Slurry is transferred to large storage tanks.

Step 7: The slurry is heated to 80-85° C. and sampled.

Step 8: Once the temperature has reached 80-85° C., the aqueous phase is separated from the solids in horizontal centrifuges (decanters)

Step 9: The solid material (pulp) is packed in laminate bags placed in metal drums which are than sampled and labeled. The pulp contained drums are then frozen and stored in frozen conditions Step 10: Aqueous phase (serum from decanter) is sampled.

Step 11: Serum is filtered and de-aerated under vacuum in order to eliminate excess foam Step 12: Serum is stored temporarily in a large container.

Step 13: The serum is centrifuged and the sludge is sent back to Step 5.

Step 14: the serum is concentrated under vacuum in an evaporator to the desired Bx value.

The above scheme is only one example of a process for producing CTC, and various other processes may also be used, without deviating from the scope of the present invention. However, the key stages of this process may be summarized as follows: Crushed tomatoes are separated into two fractions—serum and pulp—. The tomato serum is concentrated to Brix value between 40 and 80, preferably higher than 55° Bx. This product, which consists of Clear Tomato Concentrate, is commonly referred to as CTC.

Further information concerning the preparation and properties of CTC may be found in co-owned WO 99/60868, which is incorporated herein.

As explained herein above, the CTC of the present invention is subjected to heat treatment. While several different heating regimes may be used to prepare the aforementioned heat-treated CTC, in one preferred embodiment, the CTC (at a concentration corresponding to approximately 60 Bx) is heated at 90 degrees C. for a period of between 1 and 3 hours. In a particularly preferred embodiment, heat-treated CTC is prepared by heating CTC for 1 hour at 90 degrees C.

Preferred daily amounts of the heated CTC present in the compositions that are administered to subjects in need of such treatment are in the range of 100 to 500 mg.

Preferred daily amounts of total carotenoids in the compositions containing both heat-treated CTC and carotenoids, which are administered to subjects in need of such treatment, are in the range of 2 to 20 mg.

Preferably, in the compositions containing both heat-treated CTC and carotenoids, the carotenoids are present at a concentration of at least 0.1%. In one preferred embodiment of the invention, the combination compositions (i.e. those compositions containing both heated-CTC and carotenoids) comprise lycopene at a concentration of at least 0.1%.

The composition of the present invention may be formulated for either systemic or topical use. In the case of systemic administration, the heat-treated CTC may be incorporated into oral dosage forms such as tablets, caplets, capsules, syrups, elixirs, liquids etc.

In other preferred embodiments, the composition of the present invention may be administered topically, for example on the skin or mucous membranes (e.g. as creams, lotions, ointments etc.). Further details of suitable methods of incorporating the heat treated CTC-containing compositions of the present invention into the various different dosage forms may be obtained from any standard reference work known to the skilled artisan, including, for example, Remington's Pharmaceutical Sciences, Mack Publishing Co. Easton, Pa., USA (1980).

In other preferred embodiments, the composition of the present invention is prepared as a food additive that is suitable for direct incorporation into a foodstuff or a beverage.

The following examples are provided for illustrative purposes and in order to more particularly explain and describe the present invention. The present invention, however, is not limited to the particular embodiments disclosed in these examples.

Example 1

Inhibition of Production of NO Using Heat-Treated CTC

Methods and Materials:
Macrophage Isolation and Cell Culture—

Peritoneal macrophages were collected from the peritoneal cavity of 6-8 week old male ICR mice (Harlan, Israel) that had been given an intraperitoneal injection of 1.5 ml of thioglycollate broth (4%) 4 days before harvest. Peritoneal macrophages were washed three times with PBS and, if needed, a hypotonic lysis of erythrocytes was performed, yielding 90-95% purity. The macrophages were identified by FACS analysis using FITC-conjugated rate anti-mouse F4/80 (MCA497F) (Serotec, Oxford, England) by flow microfluorimetry on FACS (Becton Dickinson, Mountain View, Calif.). For each sample, 10,000 light scatter-gated viable cells were analyzed. Peritoneal macrophages were cultured in RPMI 1640 medium contained 10% FCS, 2 mM L-glutamine; 100 U/ml penicillin; 100 µg/ml streptomycin (Beit-Haemek, Isreal) in 96-well plates ($1\times10^6$ cells/well) at 37° C. in 5% $CO_2$ atmosphere. Cells were stimulated with LPS (1 µg/ml) in the presence or absence of heated CTC.

Appropriate volumes of DMSO (0.1-0.2%) were added to the controls and the percent inhibition in each test tube was calculated in relation to its control.

Clear tomato Concentrate (CTC) was prepared as described hereinabove, and since it is water soluble, was added directly to warm culture medium at the desired dilutions.

Unless otherwise stated, the heat-treated CTC used in this study refers to CTC that was heated to 90 degrees C. for period of one hours.

NO Production Assay—

NO levels in supernatants of cell cultures were determined by assaying nitrite levels using Griess reagent and sodium nitrite as a standard as described in Green, L. C., Wagner, D. A., Glogowski, J., Skipper, P. L., Whishnok, J. S., and Tannenbaum, S. R. (1982) *Anal Biochem.* 126: 131-138.

Statistical Analysis—

Data are presented as the mean±SEM. Statistical significance for comparisons between groups was determined using Student's paired two-tailed t test.

Results

A. Dose Dependent Inhibition of NO Production by CTC or Heated CTC

As shown in FIG. 1, addition of CTC or heat-treated CTC in different dilutions to the macrophages 1 before addition of 1 mg/ml LPS for 24 h, caused a dose dependent inhibition, which was significantly much more efficient in the case of heat-treated CTC.

Figure 1B:
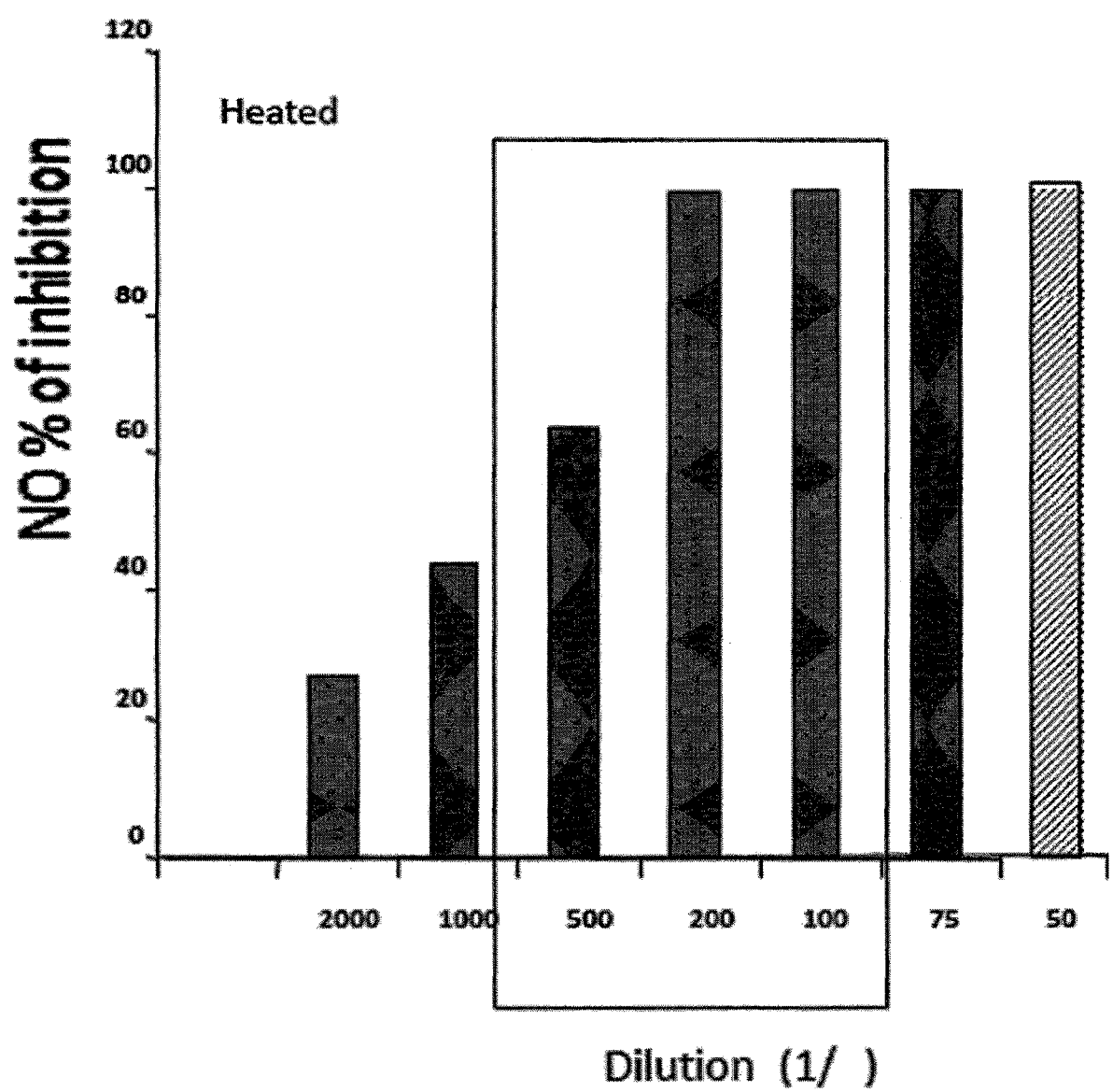

As seen in FIG. 1A, the inhibition by (untreated) CTC was first observed at 1:200 dilution and caused 16±4% inhibition while maximal inhibition of 100% was achieved by 1:25 dilution of CTC.

The inhibition by the heat-treated CTC (FIG. 1B) was much more marked than that caused by non-heated CTC at the same concentration. Even at a dilution of 1:8000 (data not shown) a slight inhibition of 3.5±1.5% was detected. At a 1:2000 dilution the inhibition observed was greater than 20%, a dose-dependent increase in efficacy being seen up until a dilution of 1:200, at which point maximum (100%) inhibition of NO production was observed.

Example 2

Determination of Optimal Heat-Treatment Conditions

Figure 2:
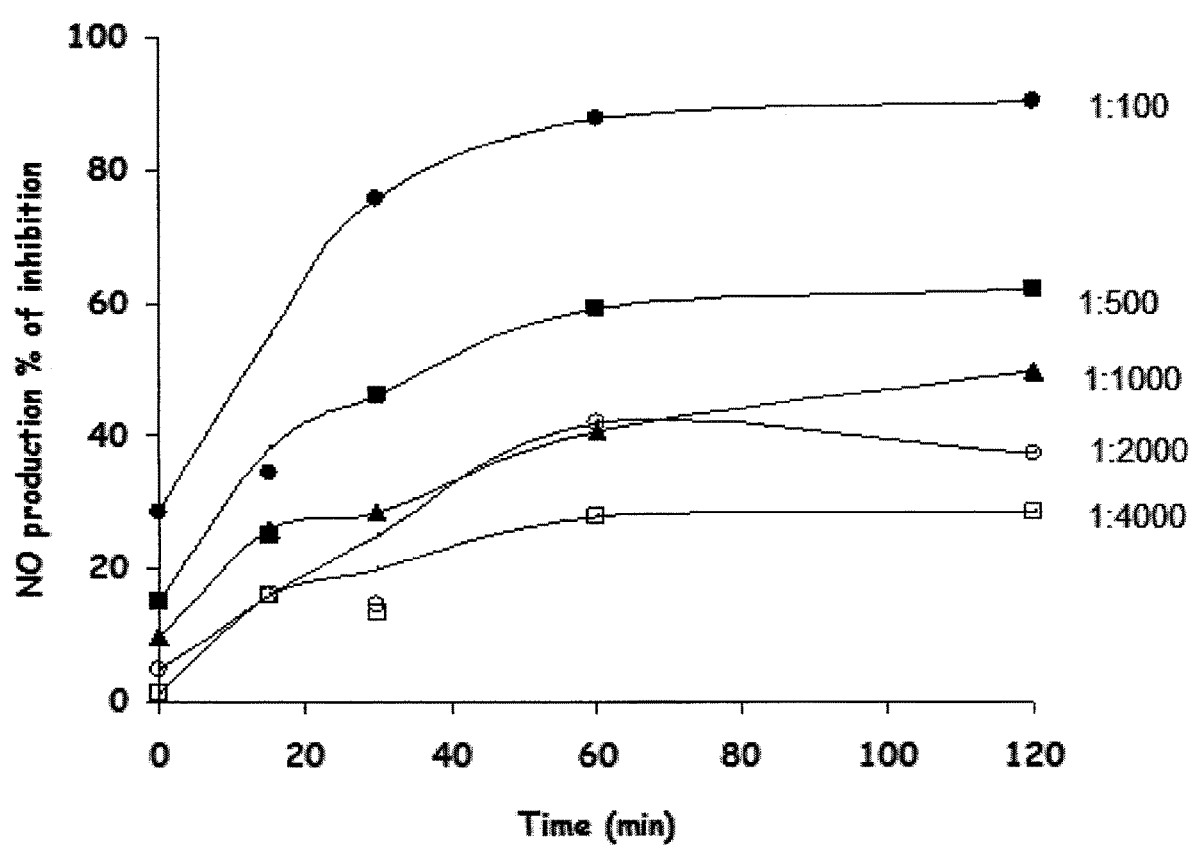
FIG. 2 graphically illustrates the effect of different heating times (0-120 minutes) on the ability of heat-treated treated CTC to inhibit NO production by peritoneal macrophages.

In order to investigate the length of heating-time needed to produce a maximum increase in anti-inflammatory efficacy, CTC was heated to 90° C. for different time durations before being added to the macrophages. As shown in FIG. 2, 1 h of incubation is sufficient to achieve maximal inhibition of NO production for all of the different CTC dilutions tested.

Example 3

Characterization of Heat-Treated CTC

The concentrations of certain key constituents of heat-treated CTC were determined and compared with the levels of said constituents in regular CTC that has not been subjected to heat treatment.

A) Amino-Acids

The concentrations of various free amino acids in CTC samples (heated and unheated) were determined using a reverse-phase HPLC method. A Zorbax Eclipse XDB-C8 column was used for the separation of Fmoc derivatizated amino acids, in which an acetate buffer/acetonitrile gradient was used as the mobile phase, at a flow rate of 1.5 ml/min. The eluted components were detected and quantified using a 265 nm UV detector.

The CTC samples (heated and unheated) were prepared as follows: One gram of CTC was diluted in a 0.2 molar base solution (prepared by dissolving 16.8 g of sodium bicarbonate in one liter of water. 0.5 ml of the diluted CTC was then transferred to a clean vial, to which a 0.5 ml of a standard amino solution was added (prepared by dissolving 20 to 40 mg of each amino acid standard in the aforementioned base solution, to a final volume of 100 ml). Nine ml of an Fmoc solution (prepared by dissolving 40 mg of Fmoc-OnSU in 100 ml of a 75% acetone/25% water mixture) was added to the vial, which was then agitated gently for 30 minutes at room temperature. In order to prevent racemization and dipeptide formation, the samples prepared as described above were analyzed within two hours following the completion of the Fmoc reaction.

A calibration curve was established using standard solutions of free amino acids treated in the same manner as the CTC samples, and used to derive the concentrations of said amino acids in the CTC samples.

The results obtained from a typical HPLC run are as follows:

|  | Gln | Glu | Ala | Phe | Ile | Leu | total |
| --- | --- | --- | --- | --- | --- | --- | --- |
| Free amino acids in Heated CTC | 0.05% | 0.53% | 0.35% | 0.12% | 0.01% | 0.01% | 1.07% |
| Free amino acids in unheated CTC | 0.89% | 0.52% | 0.32% | 0.13% | 0.02% | 0.01% | 1.88% |

These results indicate that there is a reduction in the total amount of the measured free amino acids in CTC upon heating (1.07% in heated CTC as opposed to 1.88% in unheated CTC). Furthermore, most of this reduction is due to the marked decrease in the concentration of free glutamine from a level of 0.89% in unheated CTC to 0.05% in heated CTC.

B) Sugars—Glucose and Fructose

The concentrations of glucose and fructose in CTC samples (heated and unheated) were measured using an HPLC technique.

Figure 3:
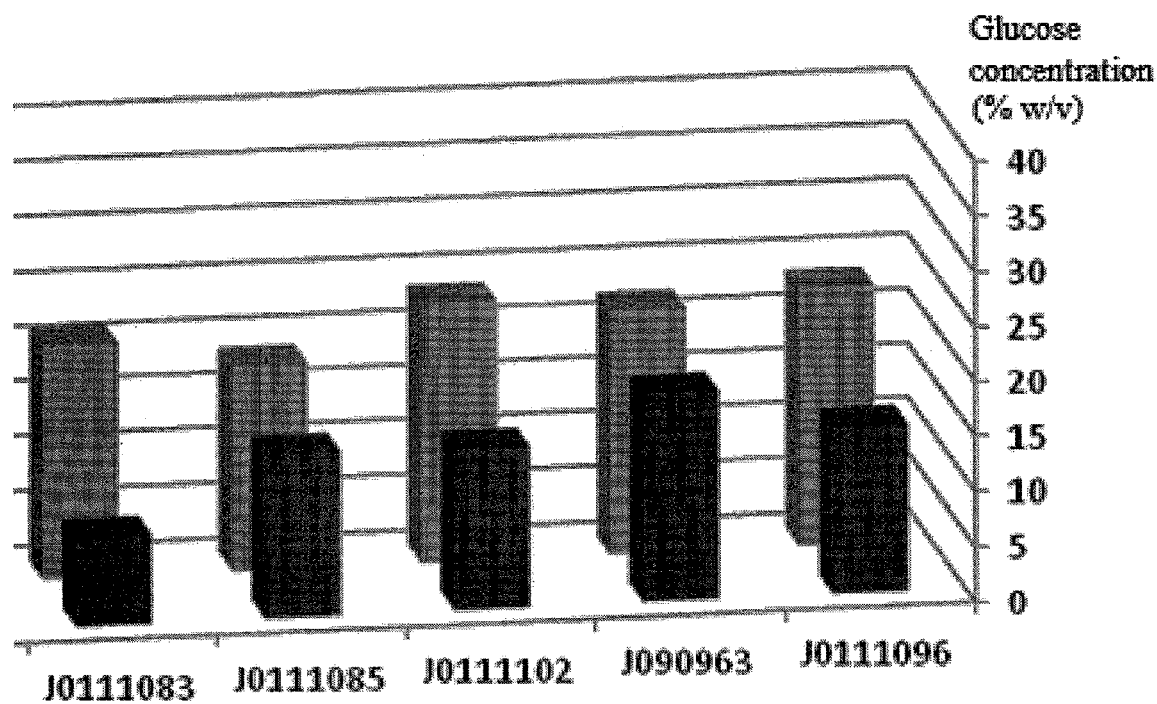
FIG. 3 graphically illustrates the concentration of glucose in each of five separate batches of CTC, both before and after heating.
Figure 4:
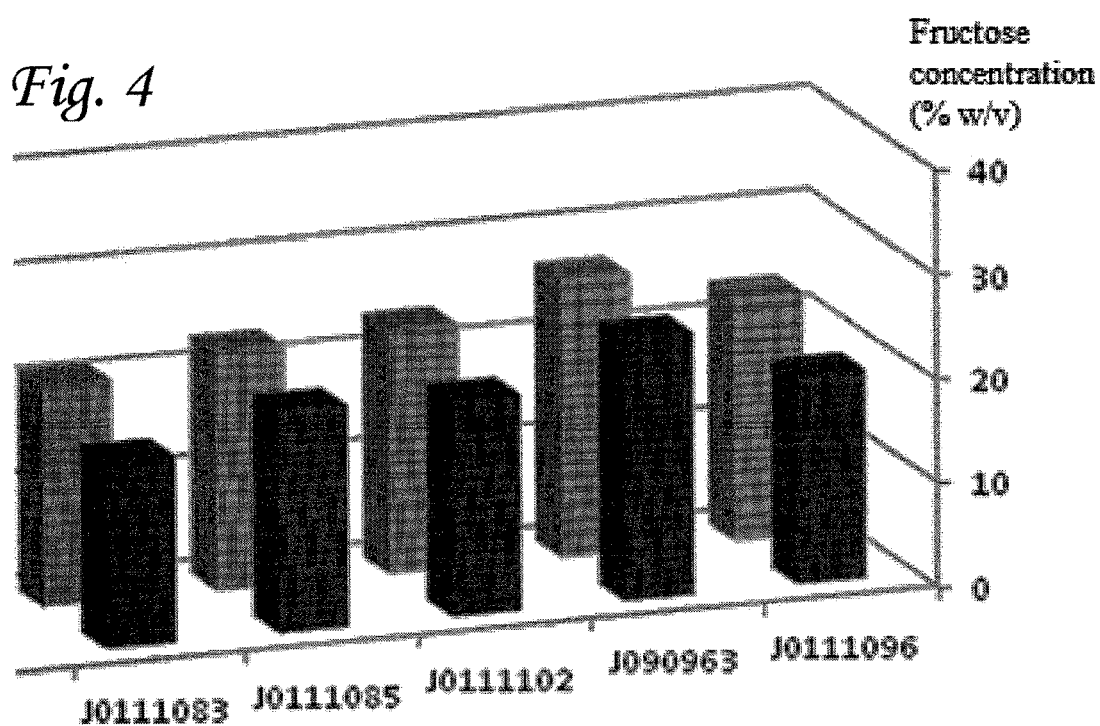
FIG. 4 graphically illustrates the concentration of fructose in each of five separate batches of CTC, both before and after heating.

The results obtained for the glucose and fructose assays in five separate batches of CTC (before and after heating) are shown in FIGS. 3 and 4, respectively. The set of bars at the front of each figure represents the results obtained for heated CTC, while the rear set represents the results obtained for non-heated CTC. It can be seen from these figures that heating a CTC sample results in a decrease of about 35% in the glucose concentration of these samples, and a decrease of about 10% in the fructose concentration.

Example 4

Inhibition of Production of TNFα Using Heat-Treated CTC

A further study was undertaken in order to determine the dose dependent inhibition of TNF-alpha production by heated CTC.

Heated clear tomato Concentrate (CTC) was prepared as described hereinabove. Macrophages were stimulated with LPS in the presence of the heated CTC, and the levels of TNF-alpha production measured (as described below) following treatment with the heated CTC.

TNF-Alpha Production Assay—

Concentrations of TNF-alpha were quantified using ELISA kits (Biolegend Inc., San Diego, Calif.).

TNFα production inhibition was observed with the concentrations of heated-CTC indicated, both when said heated-CTC was freshly-prepared and after storage for six months at either room temperate (25 degrees C.) or at an accelerated storage temperature of 40 degrees C.

Figure 5:
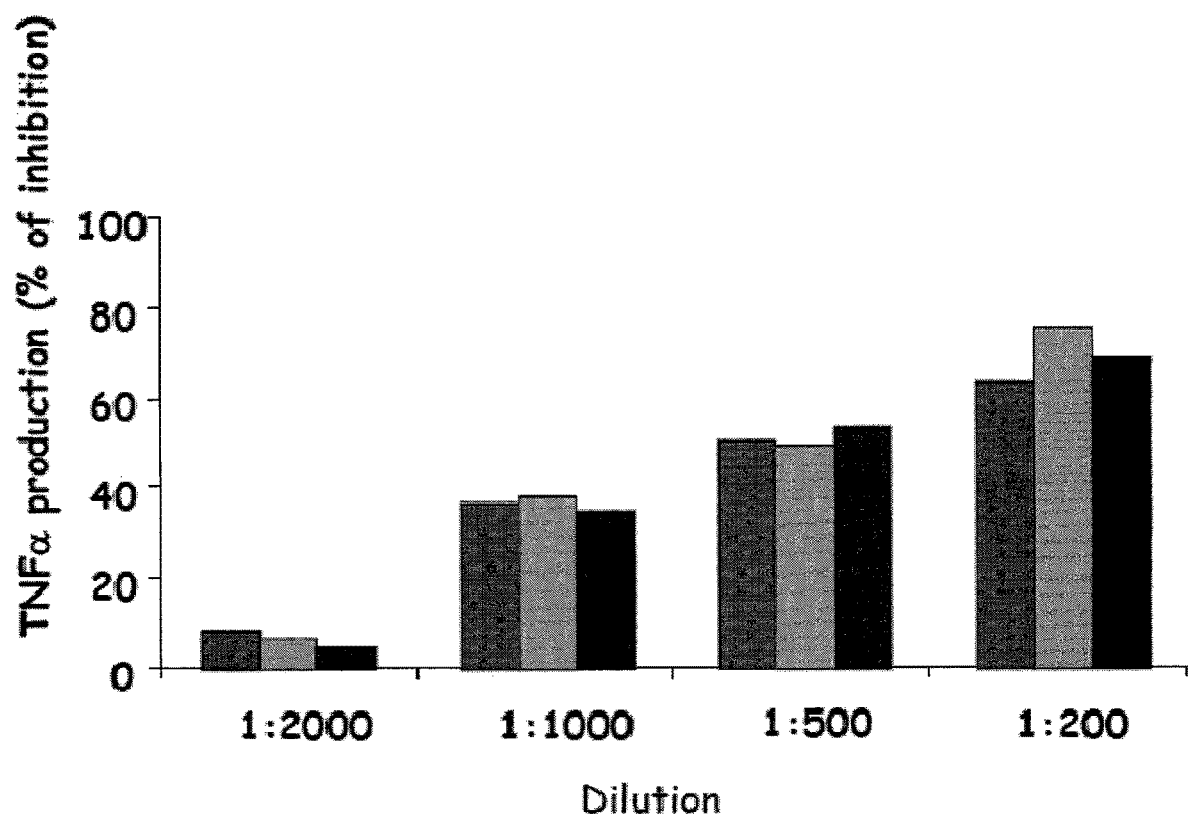
FIG. 5 shows the inhibitory effect of heat-treated CTC on TNF production by LPS-stimulated macrophages. The first of each group of three bars represents the inhibition obtained with fresh heat-treated CTC, while the second and third bars represent the results obtained with heat-treated CTC that was stored for six months at room temperature or at 40 C, respectively.

The results of this study are summarized in FIG. 5. As shown in this figure, addition of heat-treated CTC at different dilutions to the macrophages causes a dose dependent inhibition. A slight inhibition by the heated CTC was first observed at a 1:2000 dilution and was much more marked at a 1:1000 dilution. A dose-dependent increase in efficacy being seen up until a dilution of 1:200, at which point maximum (80%) inhibition of TNFα production was observed.

Further, it may be seen from the bar graph shown in this figure (first bar in each group of three bars) that at all dilutions of heated-CTC that were tested, no loss of TNFα production inhibition was observed after storage for six months at either room temperature (25 degrees C.; second bar in each group) or at an accelerated storage temperature of 40 degrees C. (third bar in each group).

Example 5

Inhibition of Production of NO Using Synergistic Combinations of Heat-Treated CTC and Carotenoids Methods and Materials:

Macrophage Isolation and Cell Culture—

Peritoneal macrophages were collected from the peritoneal cavity of 6-8 week old male ICR mice (Harlan, Israel) that had been given an intraperitoneal injection of 1.5 ml of thioglycollate broth (4%) 4 days before harvest. Peritoneal macrophages were washed three times with PBS and, if needed, a hypotonic lysis of erythrocytes was performed, yielding 90-95% purity. The macrophages were identified by FACS analysis using FITC-conjugated rate anti-mouse F4/80 (MCA497F) (Serotec, Oxford, England) by flow microfluorimetry on FACS (Becton Dickinson, Mountain View, Calif.). For each sample, 10,000 light scatter-gated viable cells were analyzed. Peritoneal macrophages were cultured in RPMI 1640 medium containing 10% FCS, 2 mM L-glutamine; 100 U/ml penicillin; 100 µg/ml streptomycin (Beit-Haemek, Israel) in 96-well plates (1×10⁶ cells/well) at 37° C. in 5% $CO_2$ atmosphere. Cells were stimulated with LPS (1 µg/ml) in the presence or absence of Lycomato or CTC and their combinations.

In some experiments, Lyc-o-Mato was dissolved in DMSO (to a final concentration of 5 mM). The mixture was vortexed and incubated in a water bath at 37° C. (with shaking) for 10 min and then sonicated in a sonicator bath three times for 15 seconds each time. Using this stock solution the desired concentrations were prepared by the addition of appropriate volumes thereof to warm culture medium.

The concentration of lycopene in the solution was determined after extraction as follows: 0.5 ml isopropanol+1.5 hexane/dichloromethane (1:5 V/V) containing 0.025% BHT were added to 1 ml of lycopene solution freshly prepared at a concentration of 200 uM in preheated medium. The solution was vortexed and the phases were separated by centrifugation 3000 rpm for 10 min.

A spectrum analysis is conducted to measure the content of lycopene (absorption peak at 471 nm.)

In other experiments, purified beta-carotene or lutein were used in combination with the heated CTC. Stock solutions and dilutions of each of these carotenoids were prepared as described hereinabove in relation to Lyc-O-Mato.

Appropriate volumes of DMSO (0.1-0.2%) were added to the controls and the percent inhibition in each test tube was calculated in relation to its control.

Clear tomato Concentrate (CTC) was prepared as described hereinabove and, since it is water soluble, was added directly to warm culture medium at the desired dilutions.

Unless otherwise stated, the heat-treated CTC used in this study refers to CTC that was heated to 90 degrees C. for a period of one hour.

NO Production Assay—

NO levels in supernatants of cell cultures were determined by assaying nitrite levels using Griess reagent and sodium nitrite as a standard as described in Green, L. C., Wagner, D. A., Glogowski, J., Skipper, P. L., Wishok, J. S., and Tannenbaum, S. R. (1982) *Anal Biochem.* 126: 131-138.

Statistical Analysis—

Data are presented as the mean±SEM. Statistical significance for comparisons between groups was determined using Student's paired two-tailed t test.

Results

Synergistic Inhibition of NO Production by Combinations of Lycomato with Heated CTC.

Figure 6:
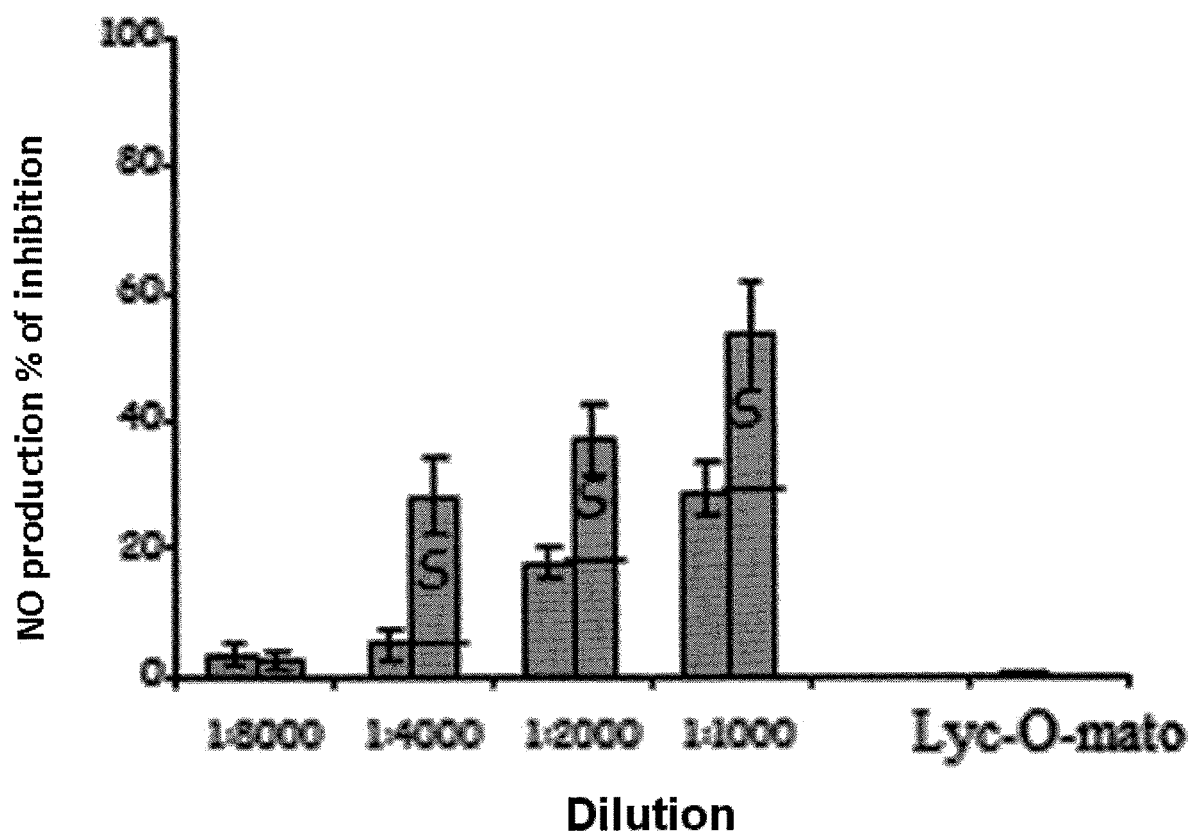
FIG. 6 graphically compares the inhibition of NO production by peritoneal macrophages caused by tomato oleoresin (Lyc-O-Mato) alone and heated CTC alone, with a combination of tomato oleoresin and heated CTC.

As shown in FIG. 6, there is synergistic inhibition of NO production by LPS treated macrophages by combinations of heated CTC in the range of 1:4000 to 1:1000 dilutions with 0.2 µM Lyc-O-mato. The first bar in each pair of bars in the figure represents the result obtained with heated-CTC alone, while the second bar in each pair represents the result obtained with a combination of the indicated dilution of heated-CTC and 0.2 µM Lycomato. The results shown are the mean values for three separate experiments, each performed in triplicate.

The greatest synergistic effect was obtained by a combination of CTC dilution of 1:400 with 0.2 µM Lycomato that caused 28.1±6% inhibition. Heated CTC (1:4000) alone caused 4.9±2.1% inhibition and 0.2 µM lycomato caused negligible inhibition. Thus the effect of this combination was 5.7 fold higher than the additive effect of each of the ingredient.

Synergistic Inhibition of NO Production by Combinations of Lutein with Heated CTC.

As shown in FIG. 7, combinations of heated CTC in the range of 1:1000 to 1:7000 dilution with both 1 µM and 2 µM lutein cause synergistic inhibition of NO production by LPS treated macrophages. The results shown are the mean values for three separate experiments.

It will be noted that the greatest synergistic effect was obtained by a combination of lutein (at both concentrations tested) together with heated CTC dilutions in the range of 1:2000 to 1:5000.

Synergistic Inhibition of NO Production by Combinations of Beta-Carotene with Heated CTC.

Figure 8A:
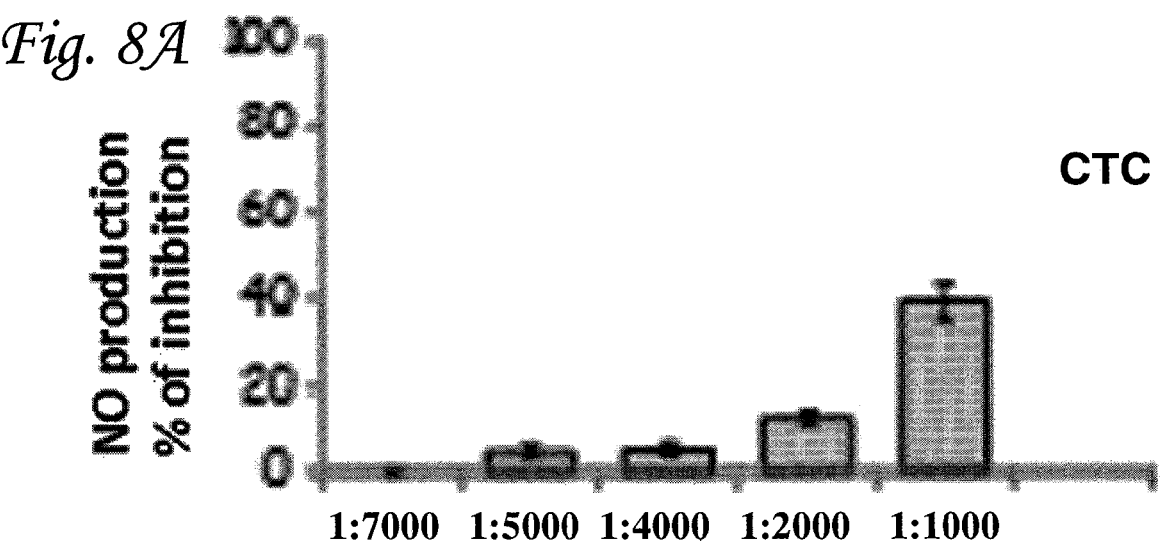
FIG. 8 graphically represent the inhibition of NO production by peritoneal macrophages caused by beta-carotene carotene alone and heated CTC alone, with a combination of beta-carotene and heated CTC.
Figure 8B:
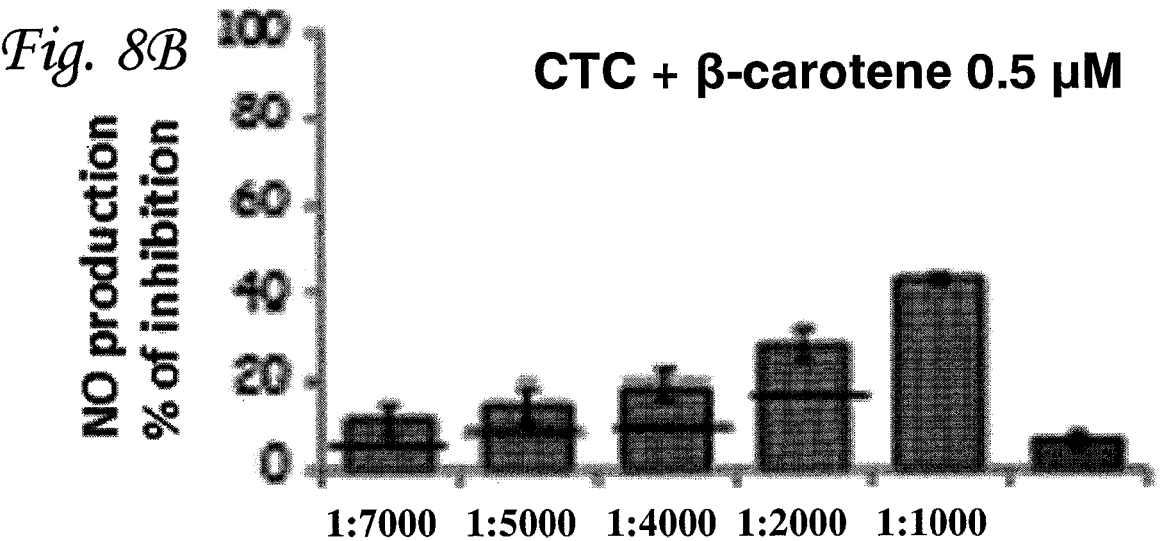
Figure 8C:
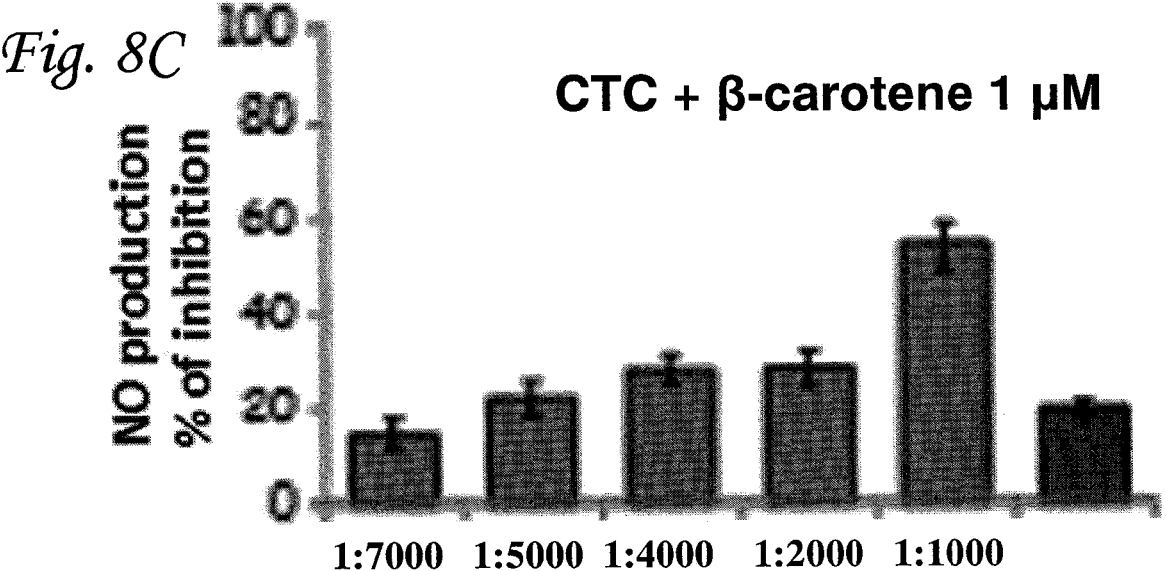

As shown in FIG. 8, combinations of heated CTC in the range of 1:1000 to 1:7000 dilutions with both 0.5 µM and 1 µM beta-carotene cause synergistic inhibition of NO production by LPS treated macrophages. The results shown are the mean values for three separate experiments.

It will be noted that in the case of 0.5 µM beta-carotene, the greatest synergistic effect was obtained by a combination with heated CTC dilutions in the range of 1:2000 to 1:7000.

These results clearly indicate that there is a synergistic interaction between heated CTC and carotenoids with regard to their ability to inhibit inflammation.

Example 6

Inhibition of Production of NO Interluekin 1-Beta Using Synergistic Combinations of Heat-Treated CTC and Carotenoids A carrageenan-induced paw inflammation model was used in order to investigate the effects of a combination of heat treated CTC and tomato oleoresin (Lyc-O-Mato; Lycored Ltd., Israel) on the production of the pro-inflammatory cytokine, IL1-beta.

Method:

Lyc-O-Mato and heat-treated CTC (prepared as described hereinabove) were administered (separately and together) by the oral route to laboratory rates, once daily, for 7 days. Diclofenac (administered i.p. two hours prior to challenge) was used as a positive control.

At day 8, a carrageenan solution was injected into the left paw of the rats. Following this injection, inflammation, mediated by the influx of neutrophils which generate ROS and pro-inflammatory cytokines, developed in the treated paw. Secretion of the pro-inflammatory cytokine, interleukin-1 beta into the inflamed tissue was measured using a standard ELISA kit.

Figure 9:
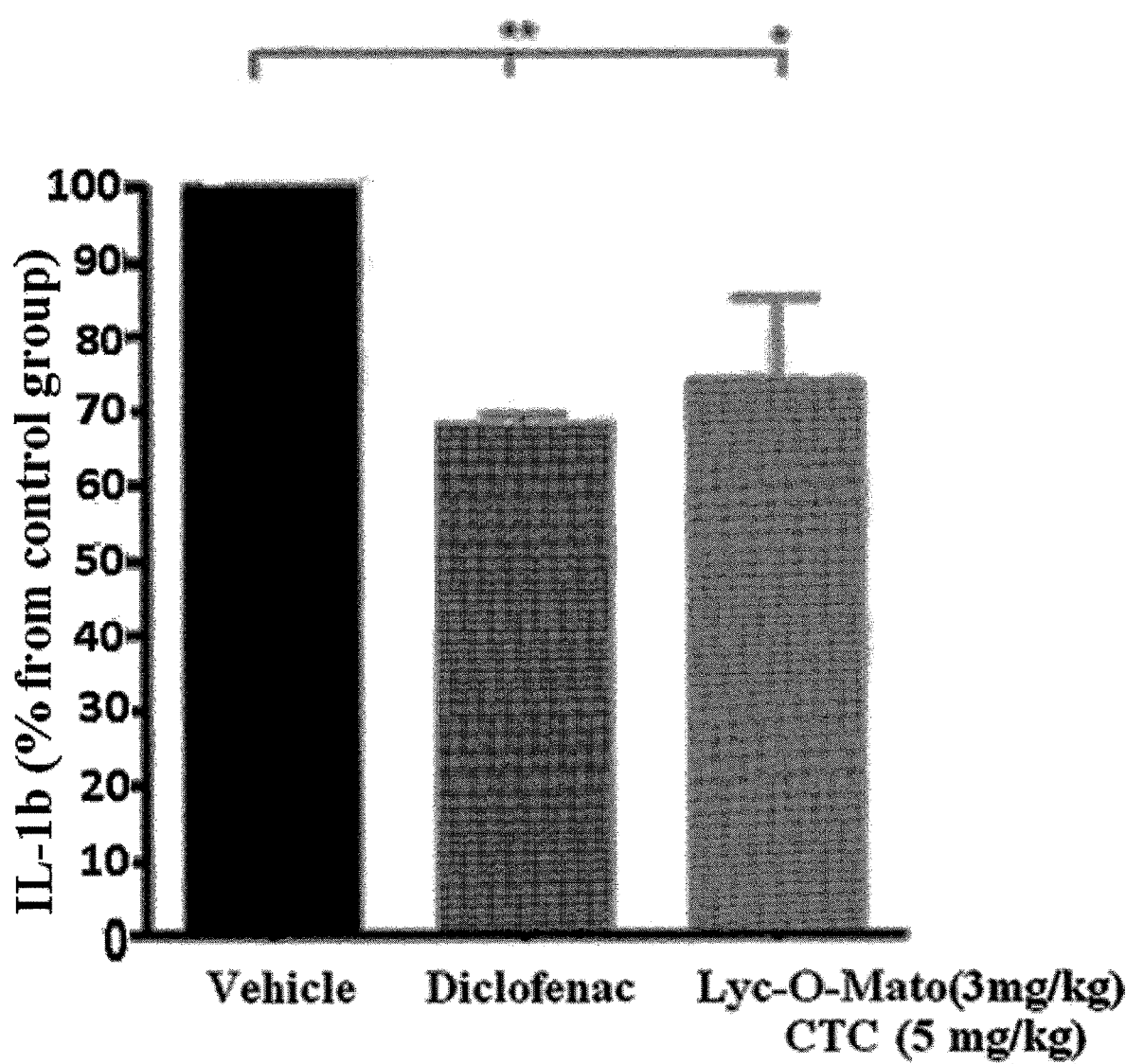
FIG. 9 graphically illustrates the inhibitory effect of a combination of Lyc-O-Mato and heated CTC on the production of interleukin 1-B in a model of carrageen-induced rat paw inflammation.

Results:

It may be seen from FIG. 9 that a combination of 3 mg/kg Lyc-O-Mato (tomato oleoresin) together with 5 mg/kg heated-CTC caused a marked and statistically significant decrease in the secretion of IL-1beta into the inflamed tissue. This decrease was similar in magnitude to that caused by the diclofenac positive control.

Example 7

The Positive Effects of Heated-CTC and Combinations of Heated-CTC and Carotenoids on Bone Health Both osteoblasts and osteoclasts are involved in bone remodeling. The present inventors have found that heated-CTC improves bone health by at least two complementary mechanisms:

1. Reduction of osteoclast differentiation.
2. Stimulation of Antioxidant Response Element signaling (ARE/NrF2) in osteoblasts.

The inhibitory effect of CTC on RANKL-mediated osteoclast differentiation and activation was studied in vitro.

Methods:

1. Osteoclast Differentiation

Cells from a mouse monocyte-macrophage cell line RAW 264.7, an osteoclast-precursors lineage, were incubated for 3 days with RANKL 20 ng/ml with or without CTC (non-heated or heated) at the indicated dilutions and stained fro TRAP activity (a marker for osteoclasts differentiation). The percent inhibition was calculated from the activity obtained in the presence of RANKL alone. LycoMato (equivalent to 1 μM lycopene) was added as indicated in FIG. 9. Data are from a representative out of 3 experiments, each performed in triplicates.

2. Measurement of Antioxidant Response Element (ARE/NrF2) Signaling in Osteoblasts Cultures of MC3T3-E1 mouse osteoblastic cells were used for this study. CTC (heated and non-heated) alone, or together with the lycopene (6, 14') oxidation product was added to the cells and ARE reporter gene transcriptional activity was measured, in accordance with the methods described in co-owned WO 2007/043046.

Figure 10:
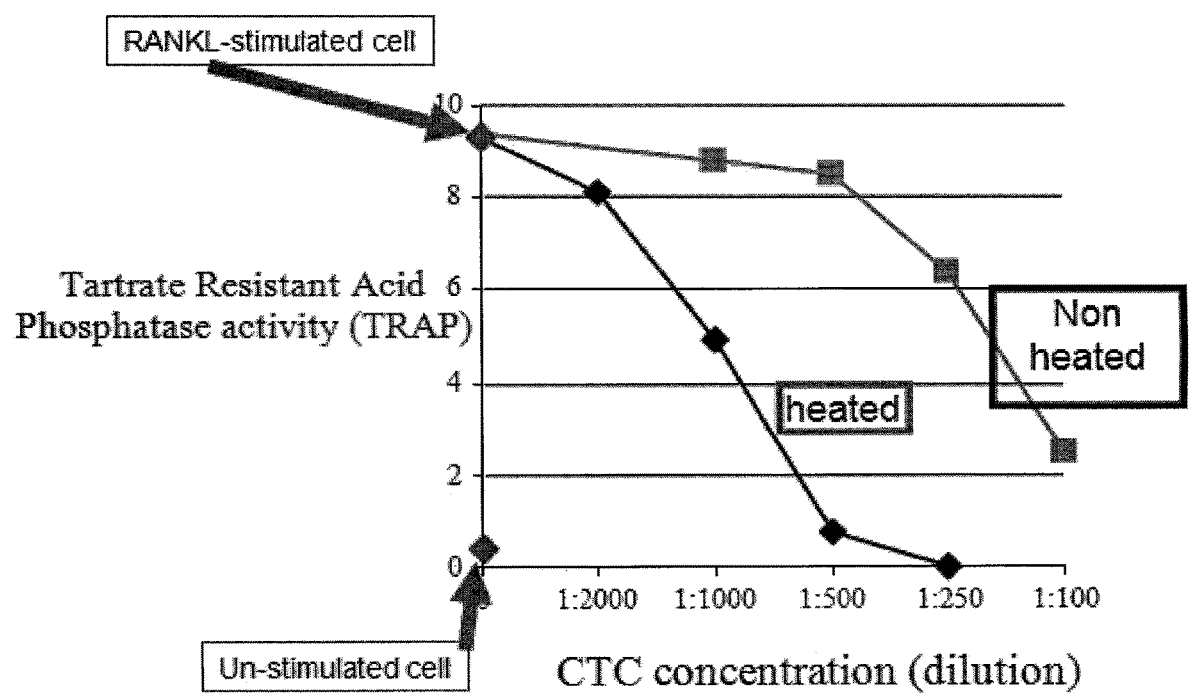
FIG. 10 graphically compares the ability of heated CTC and non-heated CTC to inhibit RANKL-induced osteoclast differentiation, as measured by Tartrate Resistance Acid Phosphatase (TRAP) activity. The results indicate that heated CTC is significantly more potent than non-heated CTC.
Figure 11:
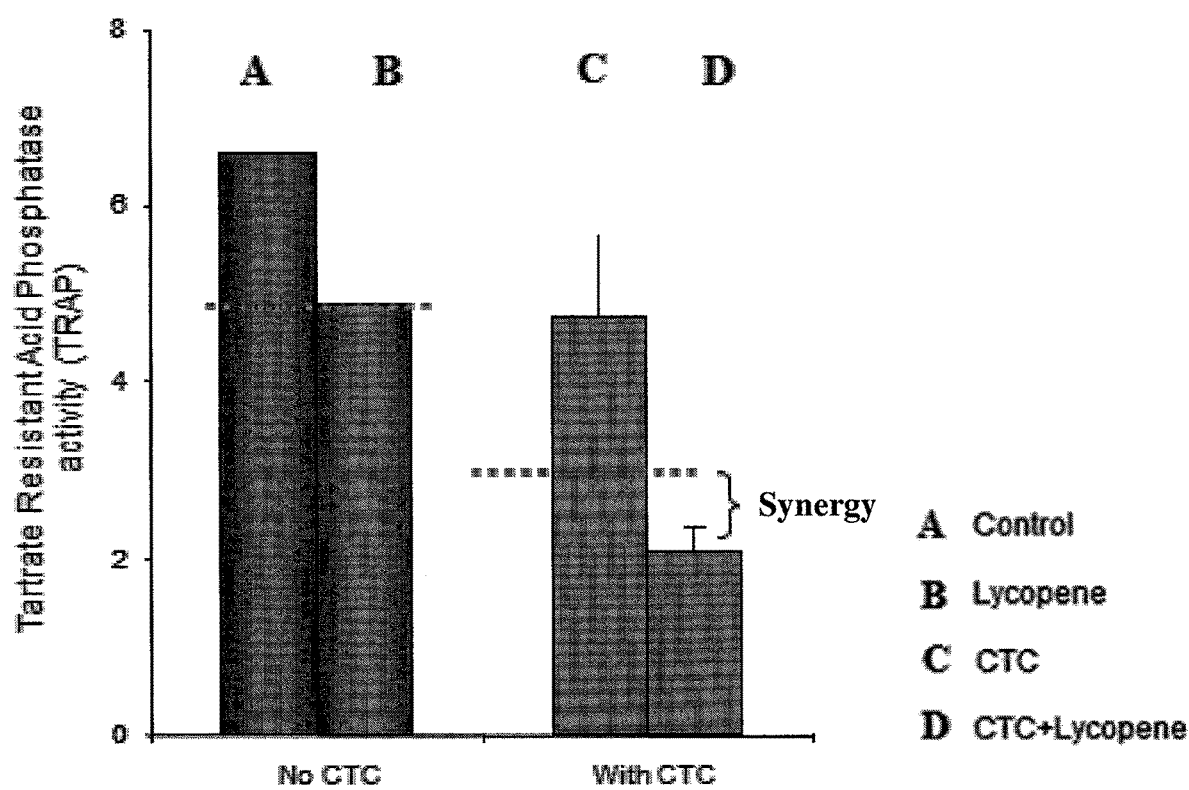
FIG. 11 graphically compares the influence of Lycopene alone with CTC alone and with Lycopene and CTC addition on the inhibition of RANKL induced osteoclast differentiation, as measured by TRAP.
Figure 12:
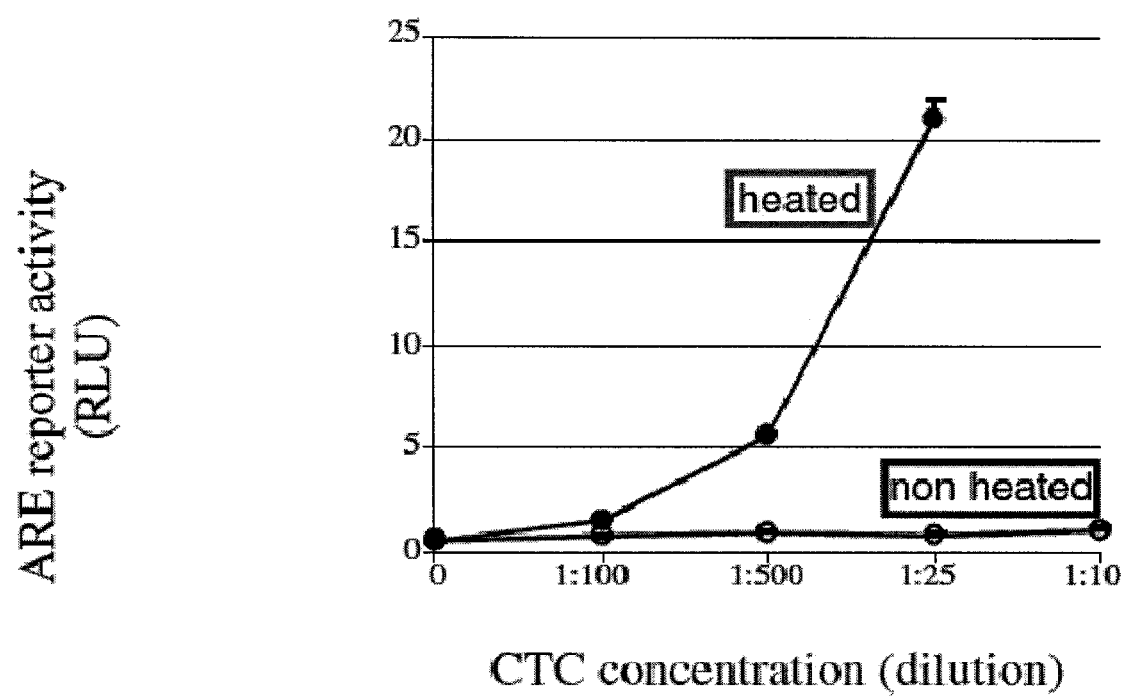
FIG. 12 graphically compares the dose dependent activation of the antioxidant response element (ARE) by heated CTC in MC3T3 osteoblastic cells with the lack of such activation that is seen with non-heated CTC.

The results of this study are summarized in FIGS. 10-12.

As shown in FIG. 10, both heated and non-heated CTC causes dose-related inhibition of RANKL-mediated osteoclast differentiation, as measured by TRAP. However, heating the CTC sample results in a significant increase in the potency of CTC in inhibition osteoclast differentiation.

FIG. 11 presents the results showing the inhibition of osteoclast differentiation caused by combinations of heat-treated CTC with lycopene. Comparison of the results of the various treatments shown in the graph indicates synergism between lycopene and heat-treated CTC.

FIG. 12 presents results showing stimulation of dose-related ARE signaling in cultured MC3T3 osteoblastic by means of treatment with heated CTC. It may also be observed that non-heated CTC has no effect in this model.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A therapeutic composition for treating inflammation comprising an effective amount of a synergistic combination of heat-treated clear tomato concentrate (CTC) and one or more carotenoids, wherein the total free amino acid concentration is less than 2% w/w, and wherein the free glutamine concentration is less than 0.1% w/w, wherein the heat treated CTC is concentrated tomato serum that is obtained by the steps of:
   (a) separating tomato material into pulp and serum,
   (b) discarding the pulp,
   (c) concentrating said serum to a Brix value between about 40 and 80, preferably above 55° Bx, and
   (d) heat-treating the concentrated serum at 90° C. for between 1 and 3 hours.

2. The therapeutic composition according to claim 1, wherein the one or more carotenoids is selected from the group consisting of lycopene, phytoene, phytofluene, beta-carotene and lutein, and/or derivatives thereof.

3. The therapeutic composition according to claim 2, wherein the carotenoid is lycopene or a derivative thereof.

4. The therapeutic composition according to claim 1, wherein the one or more carotenoids are provided by a tomato oleoresin.

5. The therapeutic composition according to claim 1, wherein the total concentration of the carotenoids in said composition is at least 0.1% (w/w).

6. The therapeutic composition according to claim 5, wherein the concentration of lycopene is at least 0.1% (w/w).

7. A method for inhibiting or reducing the production of an inflammatory mediator in a subject in need thereof, comprising administering to said subject an effective amount of the therapeutic composition according to claim 1.

8. The method according to claim 7, wherein the inflammatory mediator is selected from the group consisting of NO, TNF-alpha and interleukin 1.

9. The method according to claim 7, wherein the therapeutic composition is administered in a pharmaceutical dosage form.

10. The method according to claim 7, wherein the therapeutic composition is incorporated into a foodstuff or beverage.

11. A method of treating an inflammatory condition, comprising administering to a subject in need thereof an effective amount of the therapeutic composition of claim 1.

12. The method of claim 11 wherein NO, TNF-alpha and/or interleukin 1-beta acts as a modulator or mediator of said condition.

13. A method for improving bone health in a subject in need thereof, comprising administering to said subject an effective amount of the therapeutic composition according to claim 1.

14. The method according to claim 13, wherein the improvement in bone health comprises the inhibition of bone resorption.

* * * * *